United States Patent
Stover et al.

(10) Patent No.: US 6,486,946 B1
(45) Date of Patent: Nov. 26, 2002

(54) METHOD FOR DISCRIMINATING BETWEEN HOLES IN AND PARTICLES ON A FILM COVERING A SUBSTRATE

(75) Inventors: John C. Stover, Charlotte, NC (US); Yuri A. Eremin, Moscow (RU)

(73) Assignee: ADE Corporation, Westwood, MA (US)

(*) Notice: Subject to any disclaimer, the term of this patent is extended or adjusted under 35 U.S.C. 154(b) by 245 days.

(21) Appl. No.: 09/594,261

(22) Filed: Jun. 15, 2000

Related U.S. Application Data

(60) Provisional application No. 60/139,189, filed on Jun. 15, 1999.

(51) Int. Cl.$^7$ .......................... G01N 21/00; G01N 21/83
(52) U.S. Cl. ................... 356/237.2; 250/559.46
(58) Field of Search ................... 356/237.1–237.6, 356/429, 430; 250/559.41, 559.42, 559.45, 559.46

(56) References Cited

U.S. PATENT DOCUMENTS

| | | | |
|---|---|---|---|
| 3,749,496 A | 7/1973 | Hietanen et al. | 356/73 |
| 3,904,293 A | 9/1975 | Gee | 356/369 |
| 4,448,527 A | 5/1984 | Milana | 356/237.2 |
| 4,469,442 A | 9/1984 | Reich | 356/364 |
| 4,764,017 A | 8/1988 | Hirvonen | 356/369 |
| 4,766,324 A | 8/1988 | Saadat et al. | 250/559.41 |
| 4,794,265 A | 12/1988 | Quackenbos et al. | 250/559.45 |
| 4,889,998 A | 12/1989 | Hayano et al. | 250/559.41 |
| 4,943,734 A | 7/1990 | Johnson et al. | 250/559.18 |
| 4,966,457 A | 10/1990 | Hayano et al. | 356/239.7 |
| 4,991,445 A | 2/1991 | Le Bail et al. | 73/800 |
| 4,991,964 A | 2/1991 | Forgey et al. | 356/613 |
| 5,032,734 A * | 7/1991 | Orazio, Jr. et al. | 250/559.46 |
| 5,125,741 A | 6/1992 | Okada et al. | 356/237.2 |
| 5,189,481 A | 2/1993 | Jann et al. | 356/73 |
| 5,369,286 A | 11/1994 | Cheng | 250/559.39 |
| 5,389,794 A | 2/1995 | Allen et al. | 250/559.48 |
| 5,436,464 A | 7/1995 | Hayano et al. | 250/559.01 |
| 5,461,474 A | 10/1995 | Yoshii et al. | 356/237.4 |
| 5,465,145 A | 11/1995 | Nakashige et al. | 356/237.5 |
| 5,486,919 A | 1/1996 | Tsuji et al. | 356/484 |
| 5,625,193 A | 4/1997 | Broude et al. | 250/372 |
| 5,798,829 A | 8/1998 | Vaez-Iravani | 356/237.1 |
| 5,825,482 A | 10/1998 | Nikoonahad et al. | 356/237.2 |
| 6,108,079 A * | 8/2000 | Maeshima et al. | 356/237.2 |

FOREIGN PATENT DOCUMENTS

| | | |
|---|---|---|
| EP | 0 500 293 A2 | 8/1992 |
| EP | 0 619 601 A1 | 10/1994 |
| WO | WO92/01923 A1 | 2/1992 |
| WO | WO96/19722 A1 | 6/1996 |
| WO | WO96/22520 A1 | 7/1996 |
| WO | WO98/20327 A1 | 5/1998 |
| WO | WO98/45869 A1 | 10/1998 |

* cited by examiner

Primary Examiner—Georgia Epps
Assistant Examiner—William Choi
(74) Attorney, Agent, or Firm—Alston & Bird LLP

(57) ABSTRACT

P-polarized light or having a strong P-polarized component is directed onto a filmed substrate at two (or more) different incidence angles, one angle being relatively large and the other angle being relatively small as measured from a surface normal. Light that is scattered into a back region of the hemispherical space above the substrate surface is collected and the intensity of the collected light is measured for each of the two incident angles. A defect can be classified as either a hole in the film or a particle on the film based on the relative intensities of the collected light.

7 Claims, 13 Drawing Sheets

METHOD FOR DISCRIMINATING BETWEEN HOLES IN AND PARTICLES ON A FILM COVERING A SUBSTRATE

CROSS-REFERENCE TO RELATED APPLICATIONS

The present application claims the benefit of U.S. Provisional Application Ser. No. 60/139,189 filed Jun. 15, 1999.

FIELD OF THE INVENTION

The invention relates to optical inspection of smooth substrates having a film coating, such as silicon wafers having a dielectric film coating, in order to detect defects in the film. The invention relates more particularly to a method for discriminating between holes in the film and particles on the film.

BACKGROUND OF THE INVENTION

Progress in perfecting the basic elements of advanced computers is accomplished largely by miniaturization of the microchip structures. It follows that the standards for manufacturing of microprocessors and hard disks become more and more demanding. The production of defect-free silicon wafers is a primary goal of the semiconductor industry. High-yield manufacturing of the wafers requires decreasing both the size and fractional number of defects. As many of the wafer defects that can cause problems in manufacturing of integrated circuits cannot be visually detected, automated optical surface scanners are used for non-destructive inspection of the wafers. Optical scanners typically include a laser source of light and a system of collectors to capture the light scattered by micro defects in or on the surface being inspected. Refinement of the surface scanner design represents a prime concern for the companies developing the metrology equipment for the semiconductor industry. A lot of effort has been reported on the problem of detecting, sizing, and mapping such micro defects as surface pits and contaminating particles.

One of the less-investigated defects is a hole in a film deposited at a smooth surface of a silicone substrate. In this connection, a practical problem is the ability to distinguish a hole in a film, arising from a disturbance in the process of its manufacturing, from a contaminating particle resting on the film surface. It can be difficult to properly design and conduct experimental analyses of the light-scattering properties of film holes and particles. Accordingly, the inventors have endeavored to conduct computer simulations of the light-scattering properties of micro defects in and on plane-layered structures such as filmed silicon wafers.

The Discrete Sources Method (DSM) is an efficient and flexible tool for computer simulation of light scattering by an axisymmetric structure. The essence of the DSM consists of starting with an approximate solution of the scattering problem by representing it as a finite linear combination of the fields of dipoles and multipoles, deposited at some complementary domain. The solution constructed satisfies the system of Maxwell's equations everywhere outside medium discontinuity and infinity conditions. The amplitudes of the Discrete Sources (DS) are to be determined from boundary conditions enforced at the surface of the local obstacle causing the scattering. Thus, the scattering problem is reduced to the approximation problem of an exciting field at the obstacle surface by DS fields. A completeness of a DS fields system provides a convergence of the approximate solution to the exact one.

In prior studies, the DSM analysis has been applied to the problem of scattering of P- and S-polarized light by particles and pits on a bare silicone substrate. See, for example, Eremin, Yu. A., Orlov, N. V., *Simulation of light Scattering from Particle upon Wafer Surface*, Appl. Opt. 35 (1996) 33, 6599–6605; Eremin, Yu. A., Orlov, N. V., *Study of Scattering Properties of Defects of Silicon Wafers*, Opt. Spectr. 84 (1998) 4, 557–562. However, there is no known analysis providing a method for discriminating between particles resting on a film and holes formed in a film on a substrate.

SUMMARY OF THE INVENTION

The present invention is a result of an extension of the DSM analysis to the case of polarized light scattering by a particle located on a film or a hole formed in the film deposited on a substrate. The DSM analyses performed by the inventors suggest a convenient and efficient method and apparatus enabling optical surface scanning of a filmed substrate such as a filmed silicon wafer in order to discriminate between particles on and holes in a film. In accordance with a preferred embodiment of the invention, light that is P-polarized or at least has a strong P-polarized component is directed onto the filmed substrate at two (or more) different incidence angles, one angle being relatively large and the other angle being relatively small as measured from a surface normal. Light that is scattered into a back region of the hemispherical space above the substrate surface (i.e., scattered generally back toward the direction from which the incident beam approaches the surface) is collected and the intensity of the collected light is measured for each of the two incident angles. It has been found through DSM modeling that for holes formed in the film, the back-scattered light intensity at a relatively large incidence (i.e., highly oblique incidence) is substantially smaller than the back-scattered light intensity at a relatively small incidence (i.e., normal or near normal incidence). For particles, however, there is no such substantial decrease in intensity, and in many cases the intensity actually increases slightly from small to large incidence. Accordingly, a defect can be classified as either a hole or a particle by scanning the surface at both small and large incidence, measuring back-scattered light intensity for both incidence angles, and looking for a substantial decrease in intensity. If there is no such decrease, the defect is a particle; if there is a substantial decrease, the defect is a hole.

A suitable apparatus for carrying out the method of the present invention can include various types of collector geometries for detecting the intensity of light scattered into a back region of the hemisphere. The range of scattering angles over which collection of light was modeled by the DSM technique was −20° to −75°, and the range of azimuth angles was −177° to −120° and 120° to 177° (zero azimuth angle being defined as lying on the intersection of the incident plane with the substrate surface in the forward direction). Advantageously, in practice a semi-annular collector can be used to collect light scattered over a semi-annular portion (i.e., covering azimuth angles of about 90° to −90°) of the back half of the hemisphere and extending over a wide range of scattering angles. However, any configuration of one or more collectors capable of collecting light scattered over a relatively wide range of scattering angles and azimuth angles can be used.

The extension of the DSM technique developed by the inventors provides an opportunity to realize effective code allowing computer simulations of the light-scattering properties of film holes and particles to be readily performed. This extension of the technique in turn has led to the development of methods and apparatus that can be used to conveniently and efficiently discriminate between holes and particles on a filmed substrate.

BRIEF DESCRIPTION OF THE DRAWINGS

The above and other features, objects, and advantages of the invention will become more apparent from the following description of a preferred embodiment of the invention when taken in conjunction with the accompanying drawings, in which.

DETAILED DESCRIPTION OF THE DRAWINGS

Figure 1A:
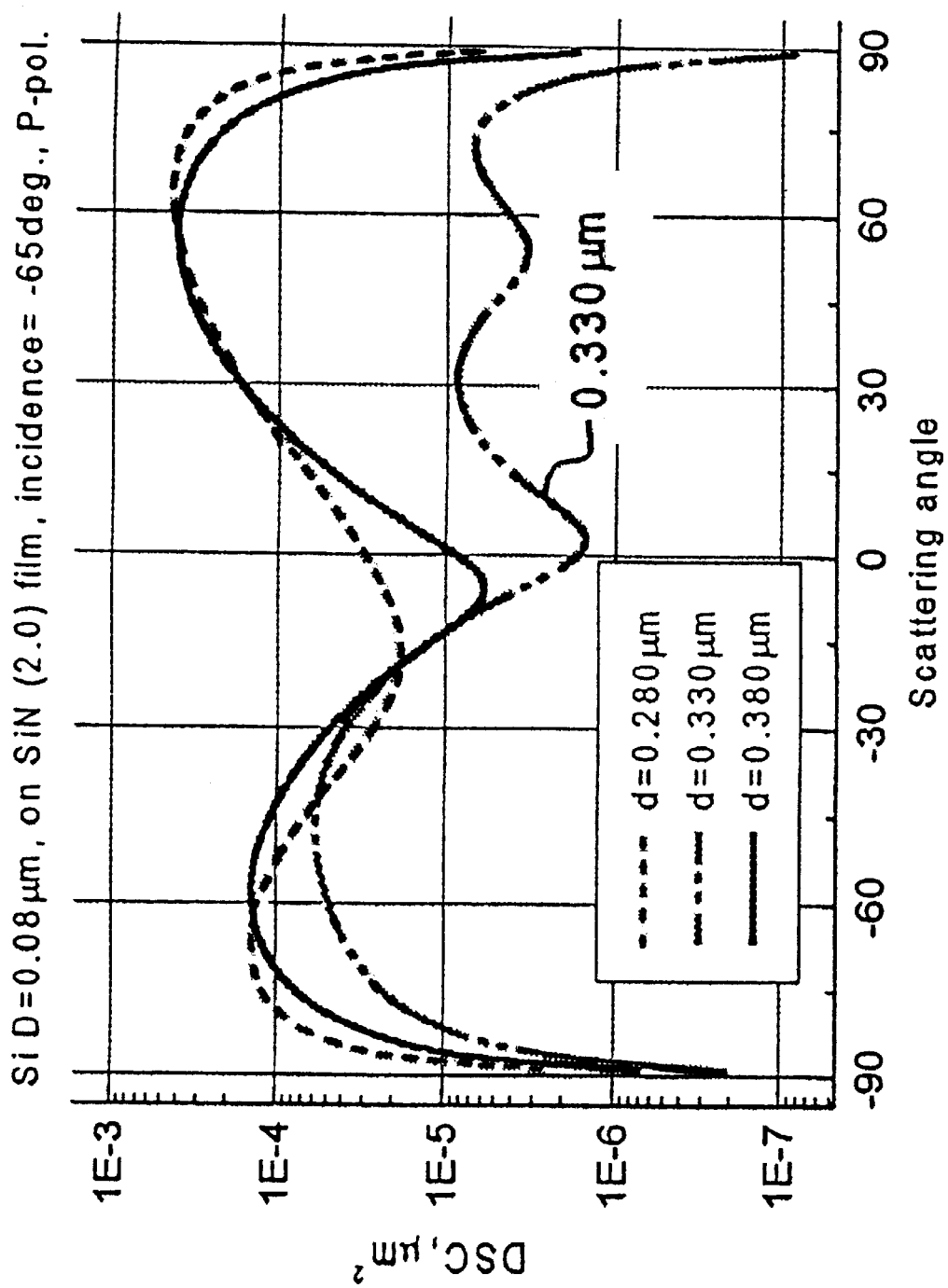
FIGS. 1a–d show results of computer simulations of the intensity or Differential Scattering Cross-section (DSC) as a function of scattering angle for P-polarized light at an incident angle of −65°, for spherical particles of silicon and aluminum of 0.08 μm diameter and for various thicknesses of three types of dielectric film materials.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The main objective of the invention is the discrimination of a contaminating micro particle (of unknown diameter and refractive index) from a hole in a surface of a film deposited on a silicon substrate. The problem is complex because the scattering characteristics depend upon many parameters. For example, the Differential Scattering Cross-section (DSC) in units of area/steradian is given by the formula $$DSC^{P,S}(\theta_0, \theta, \phi) = \frac{dP^{sca}/d\Omega}{I^{inc}} = |F_\theta^{P,S}(\theta_0, \theta, \phi)|^2 + |F_\phi^{P,S}(\theta_0, \theta, \phi)|^2$$

where $\theta_0$ is the incident angle, $\theta$ is the scattering angle measured from the surface normal, $\phi$ is the azimuth angle of the scattered light, $P^{sca}$ is the scattered power, $I^{inc}$ is the incident intensity in watts/μm², and $F_{\theta,\phi}^{P,S}(\theta_0,\theta,\phi)$ are the components of the scattering diagram. Thus, it can be seen that the DSC depends on geometry and material parameters of the defect as well as polarization of the exciting plane wave, the angle of incidence, and two scattering angles. In the computer simulations presented herein, it is assumed that there is an exciting wavelength equal to 0.488 μm and a silicon substrate having a complex refractive index of n=4.37−0.08j.

The DSC features that allow the discrimination of surface particles and pits on a bare substrate such as a bare silicon wafer are first described. As described in commonly assigned U.S. patent application Ser. No. 09/338,251 filed Jun. 22, 1999, the disclosure of which is incorporated herein by reference, particles and pits can be discriminated on such a bare substrate by using P-polarized light and oblique incidence such as $\theta_0$=−65°. In the bare substrate case, the DSC for a particle in the incident plane exhibits a dip near the surface normal direction, i.e., $\theta$=0°. However, the DSC for a pit does not have a dip in this direction. Thus, this DSC characteristic feature enables a system of collectors that detect the presence or absence of the dip and makes discrimination possible.

In the case of light scattering by a contaminating particle located on a film surface, however, the DSC has a more complex structure because the transparent film deposited on a silicon substrate works as a plane waveguide. For each film material, one can find a film thickness that drastically alters the conventional form of the DSC regardless of particle form and material. Some examples for Al (n=0.73−5.93j) and Si particles are shown on FIGS. 1a–d.

Figure 1B:
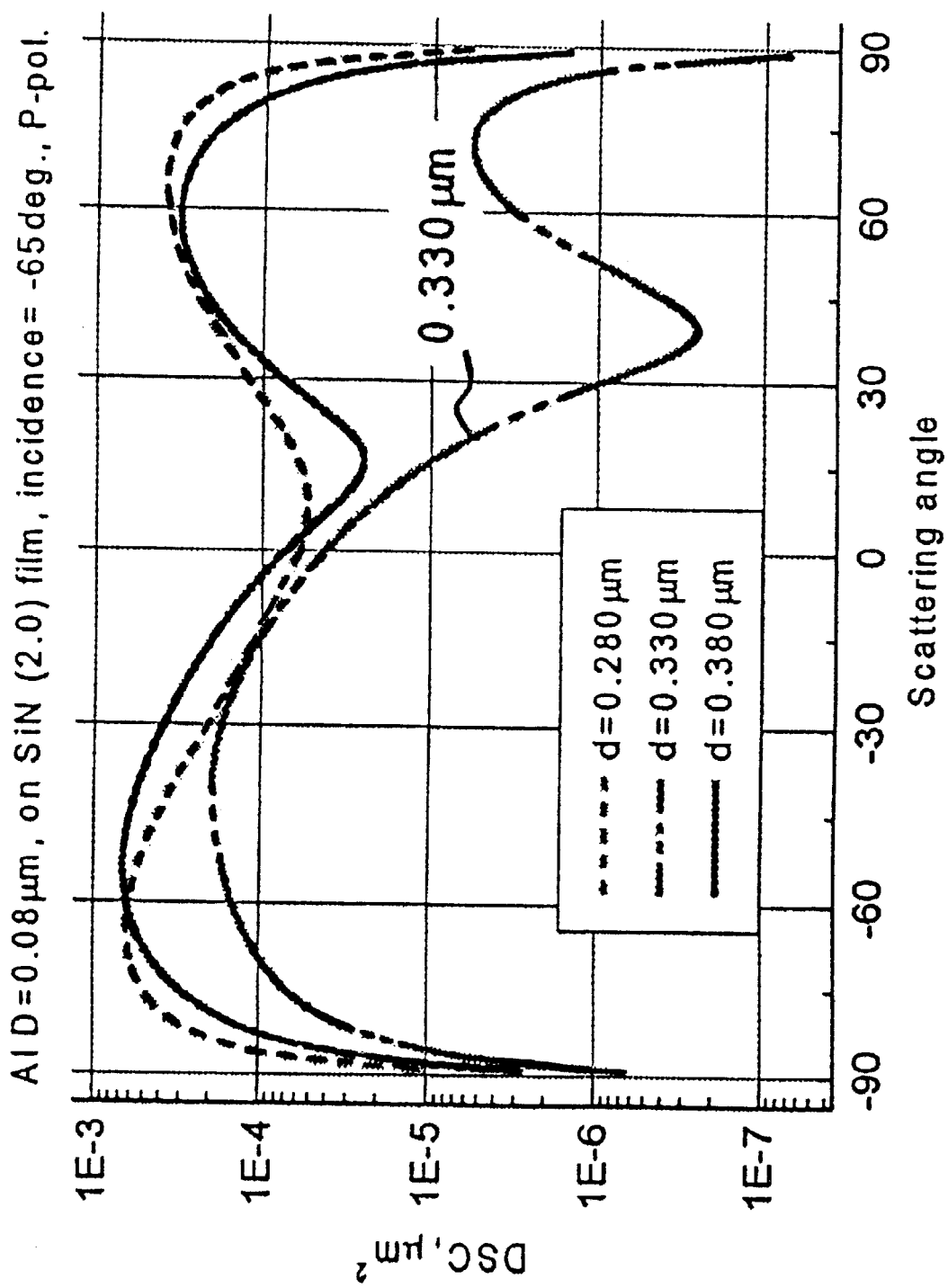
Figure 1C:
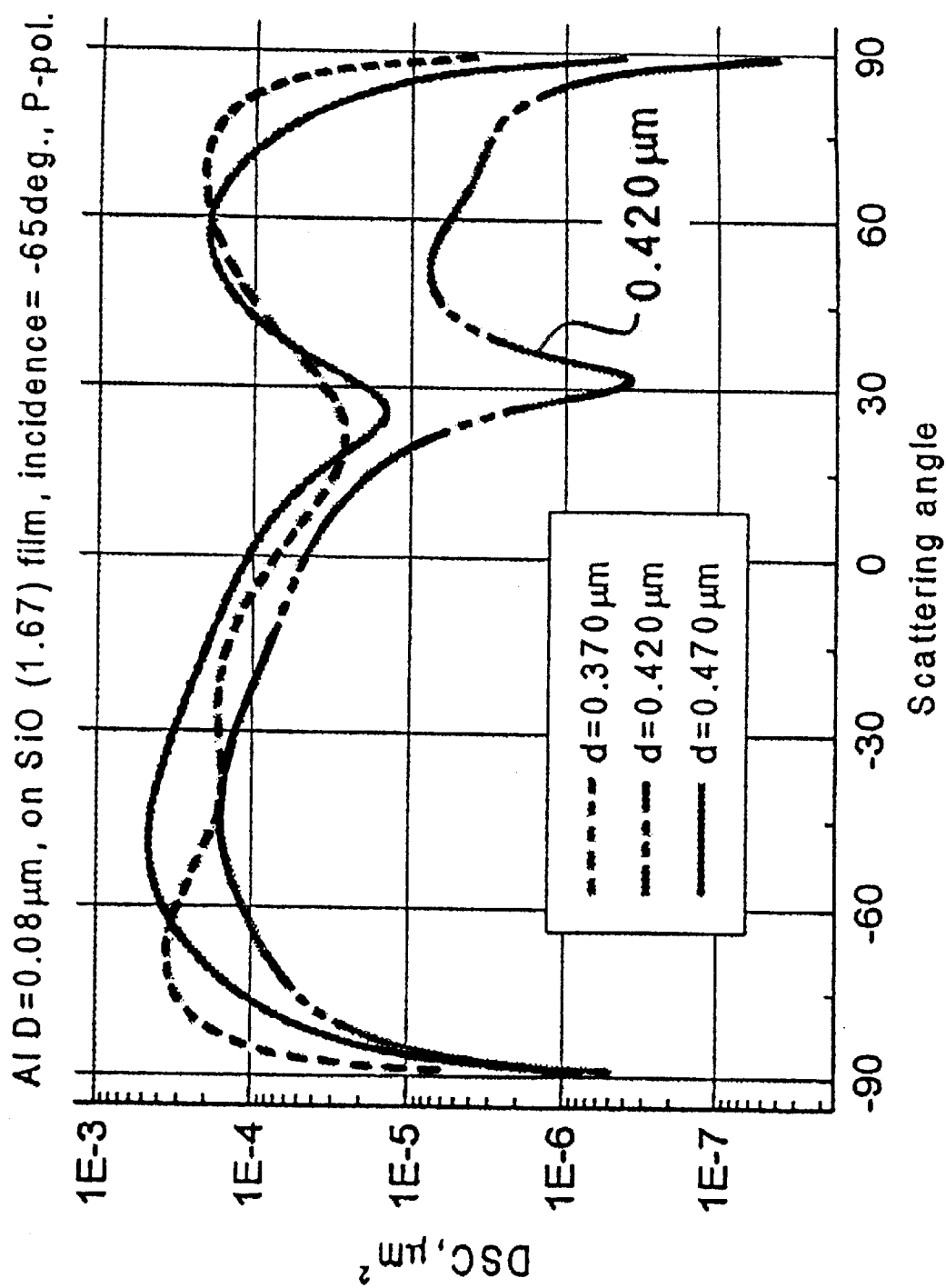
Figure 1D:
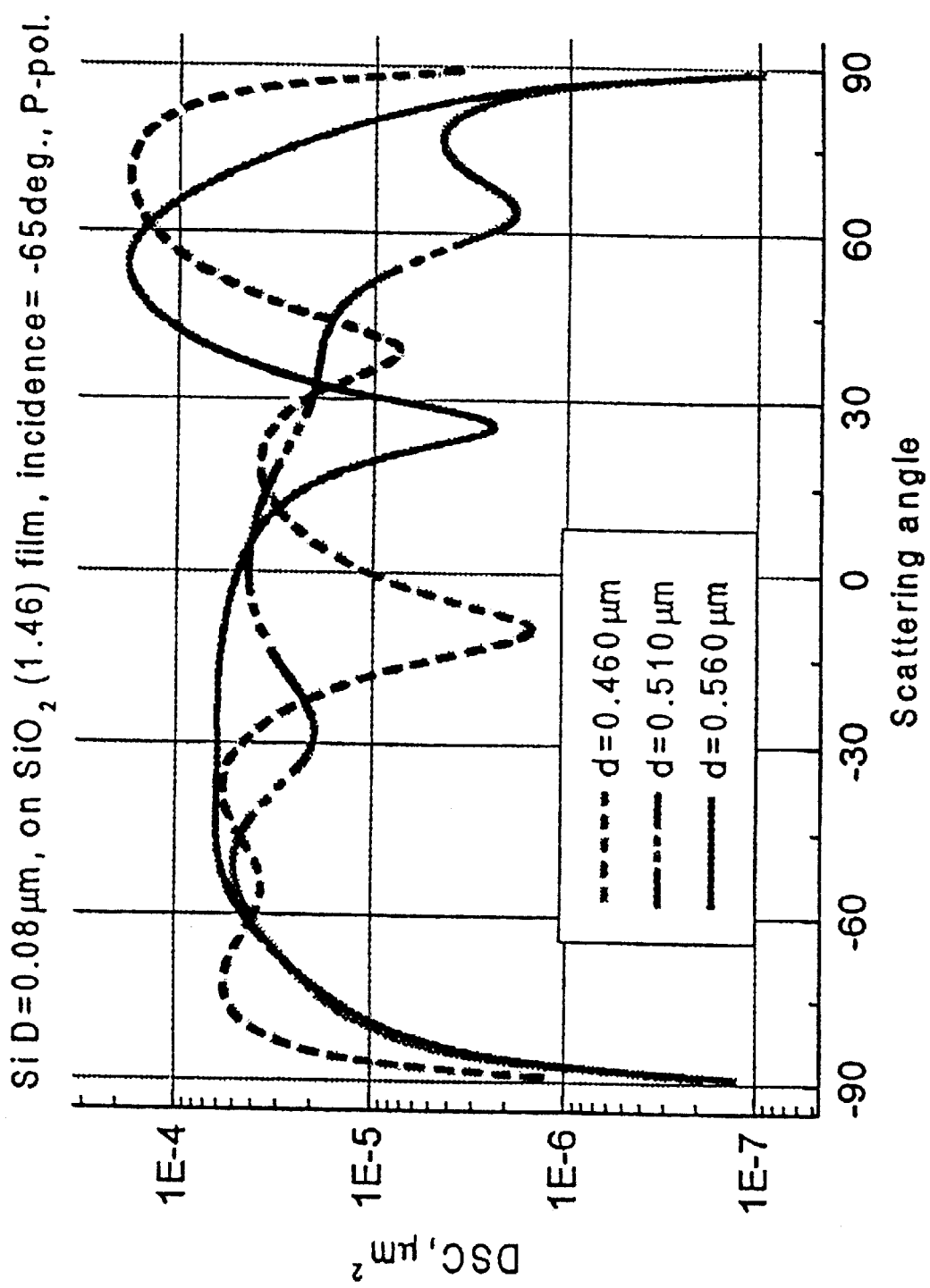

FIG. 1a demonstrates $DSC^P$ versus scattering angle in the incident plane using an incident angle of $\theta_0$=−65° for a Si sphere having a diameter of 0.081 μm located on a SiN (n=2.0) film. The various curves correspond to different film thicknesses d=0.28 μm, 0.33 μm, and 0.38 μm. Film thickness d=0.33 μm represents the "resonance" case. Similar results for an Al sphere are shown in FIG. 1b. FIG. 1c demonstrates $DSC^P$s associated with an Al sphere on a SiO (n=1.67) film. Resonance film thickness in this case is equal to d=0.42 μm. FIG. 1d corresponds to a Si particle on an SiO₂ film. In this figure, one can see more complex forms of the curves for the $DSC^P$. For a resonance case, the form of $DSC^P$ strongly differs from the non-resonance film thickness. In particular, the DSC near the specular direction (about $\theta$=65°) is greatly reduced.

Consider next the scattering from a hole in a film surface compared with the contaminating particle $DSC^P$. Results for both a cylindrical hole (D=0.15 μm) and a conical hole ($D_{upper}$=0.15 μm, $D_{lower}$=0.05 μm and $D_{average}$=0.10 μm) are shown in FIGS. 2a–d.

Figure 2A:
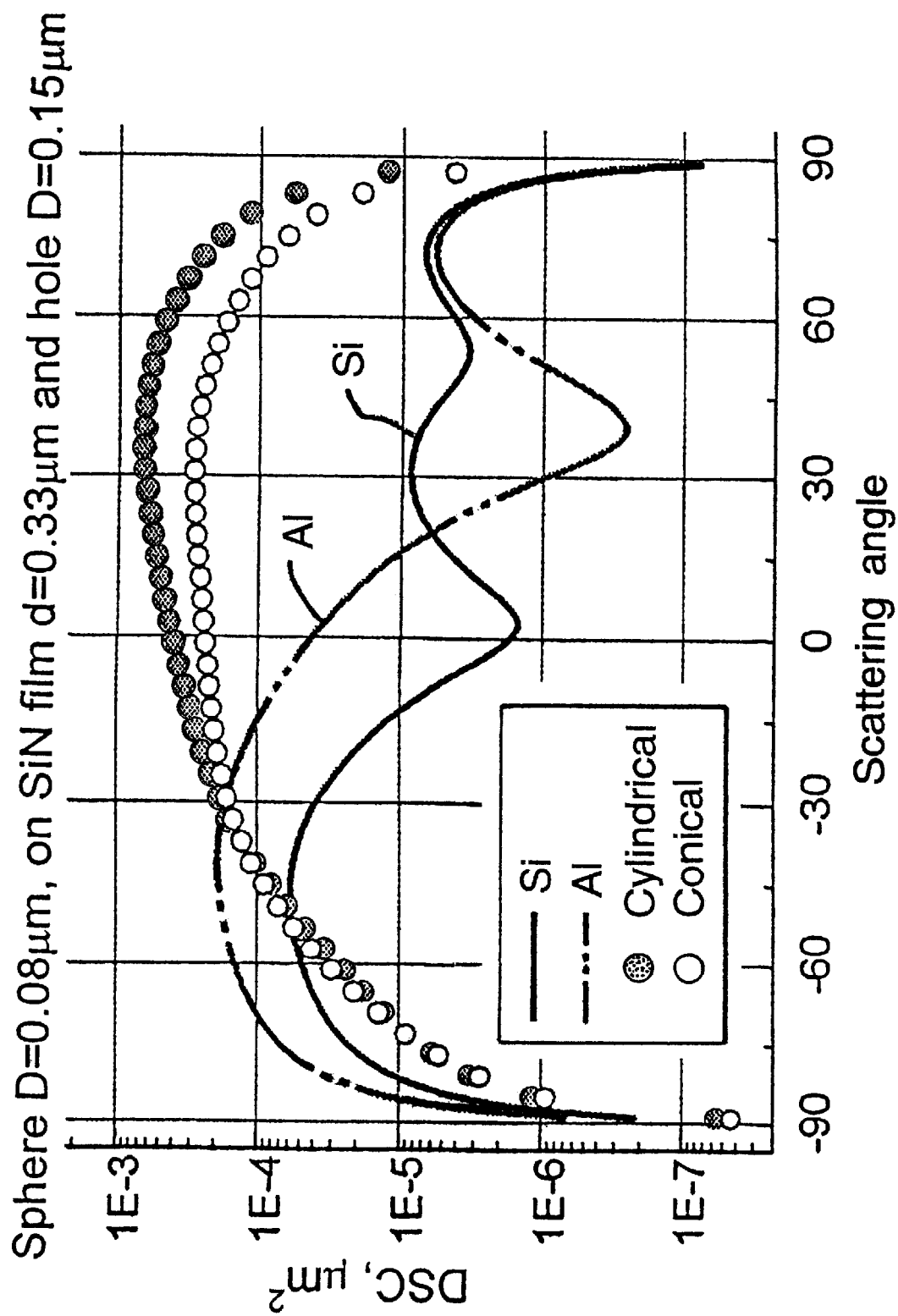
FIGS. 2a–d show computer simulation results similar to FIGS. 1a–d, but comparing DSC curves for 0.08 μm-diameter particles with DSC curves for 0.15 μm-diameter holes of both cylindrical and conical shape.
Figure 2B:
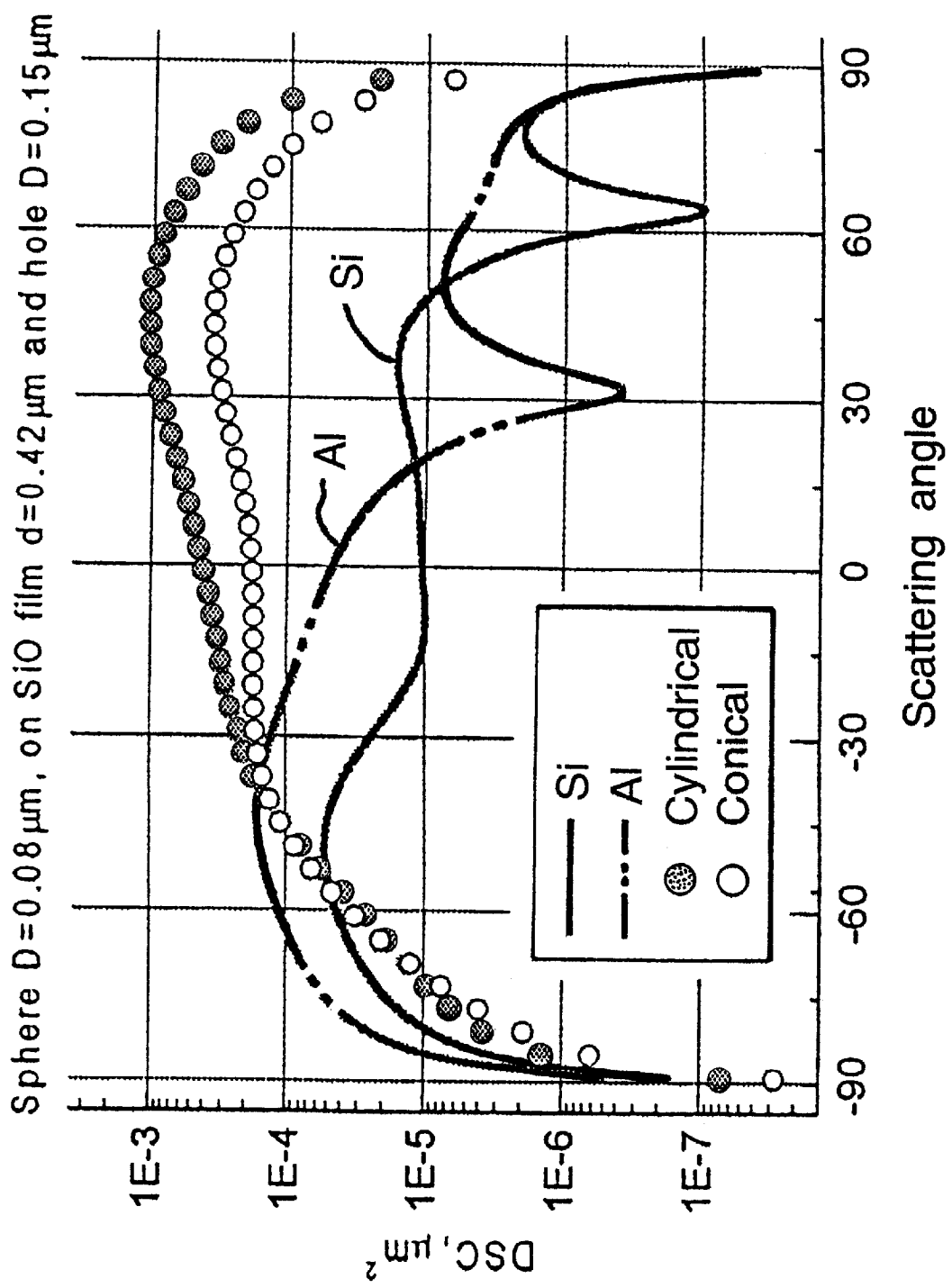
Figure 2C:
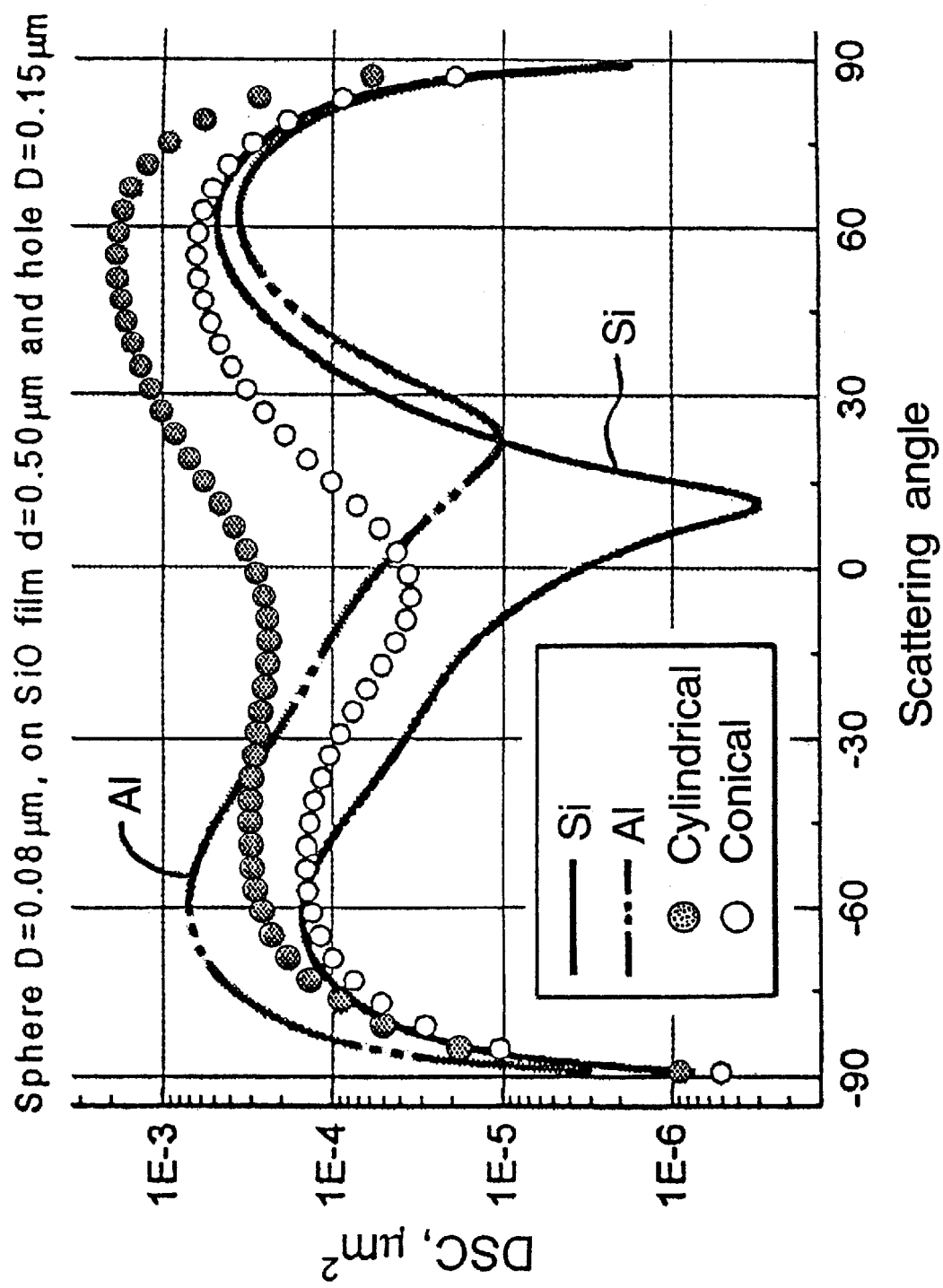
Figure 2D:
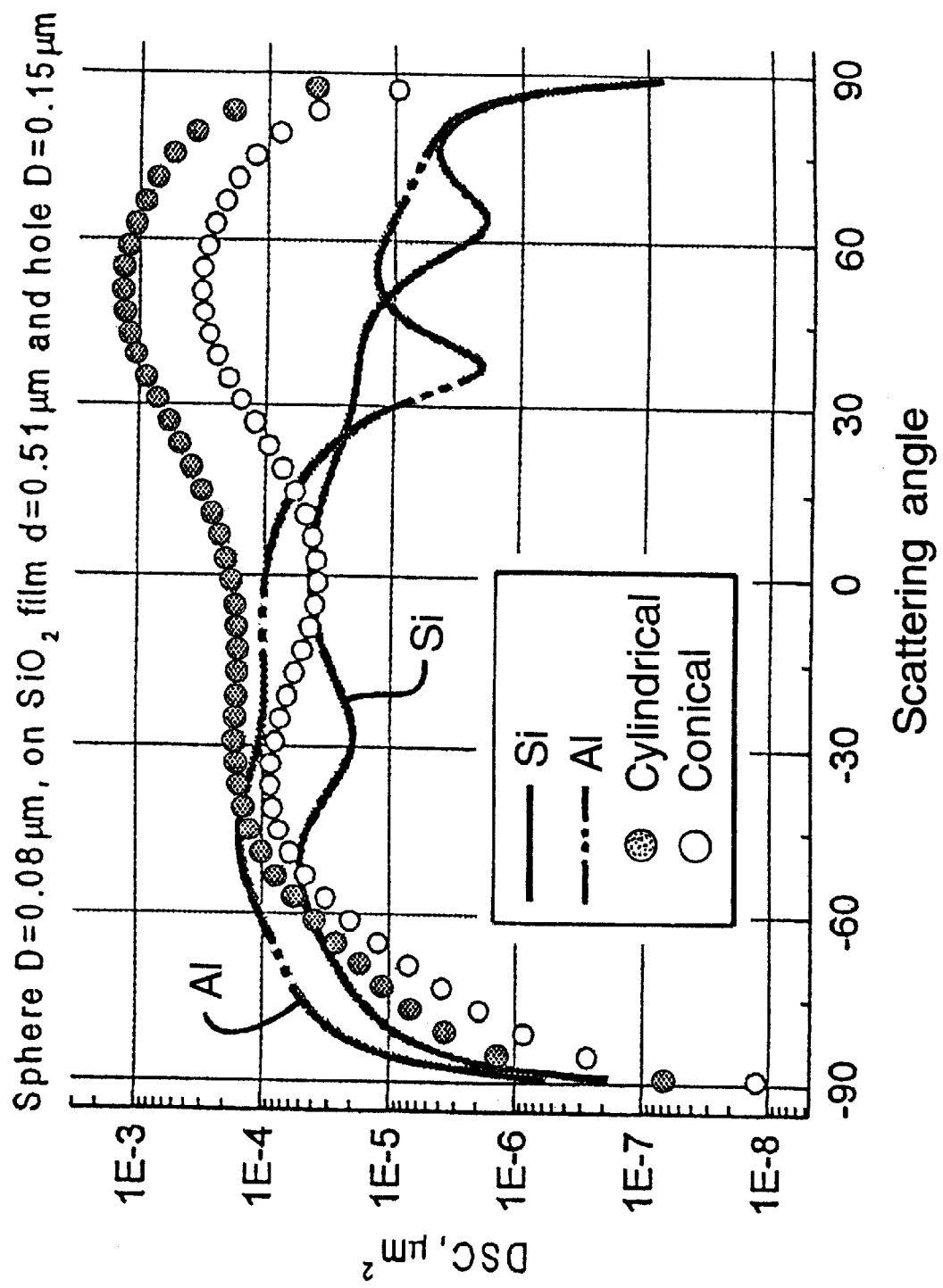

First, as can be seen by comparing the d=0.280 μm curve in FIG. 1a with the curve for the conical hole in FIG. 2c, the shape of the DSC curve for a particle on a filmed substrate may be very similar to the DSC for a hole in a filmed surface. FIGS. 2a,b and d are associated with the resonance film thickness. FIG. 2a shows DCS distributions for Al and Si particles (D=0.08 μm) compared to holes in a SiN film of thickness d=0.33 μm with an incidence of $\theta_0$=−65°. Similar results for a SiO film having a thickness d=0.42 μm are shown on FIG. 2b. FIG. 2c corresponds to a non-resonant SiO film thickness d=0.50 μm. In this figure, one can see the conventional form of DSCs for particles. The result for resonance with an SiO₂ film (d=0.51 μm) is depicted on FIG. 2d. These curves demonstrate a more complex picture of scattering. From the results observed, it can be seen that scatter for a particle deposited on a filmed substrate has a more complicated nature than scatter from a particle on a bare substrate surface. Hence, the type of collector system used to discriminate a particle from a pit on a bare substrate may fail to discriminate a particle from a hole in a filmed substrate.

Accordingly, a different measurement geometry must be employed to provide particle/hole discrimination on filmed substrates. To determine a suitable collector geometry, a response function, $R^{P,S}$, having units of area, is determined as $$R^{P,S}(\theta_0) = \int_\Omega DSC^{P,S}(\theta_0, \theta, \phi) d\omega$$

Here $\Omega$ is some portion of the reflective hemisphere, and can be considered to be the area covered by a collector used to collect scattered light. A collector is disposed near the back scattering direction and covers an area of integration corresponding to two parts of an annular ring placed symmetrically with respect to the incident plane, and defined as $\Omega = \{-20° \leq \theta - \leq 75°; -177° \leq \phi \leq -120°, 120° \leq \phi \leq 177°\}$. FIG. 4 schematically depicts one half of such a collector C on one side of the incident plane P (the other half of the collector C on the other side of the incident plane P and covering positive azimuth angles $\phi$ of 120° to 177° being omitted for clarity of illustration) disposed above a substrate S. A light source 10 is arranged to create a beam of P-polarized light, and one or more deflectors 12 are used for directing the beam onto the substrate S at an incident angle $\theta_0$. It will be understood that there are one or more detectors (not shown) associated with the collector C for measuring the intensity of the light collected by the collector. If the incident angle is varied over a range of 0° to about −80° and the response function is calculated for each incident angle, the response function can be plotted as a function of incident angle. The response functions were calculated in this manner for the same conditions used to obtain the DSC curves of FIGS. 2a–d, and the results are plotted in FIGS. 3a–d.

Figure 3A:
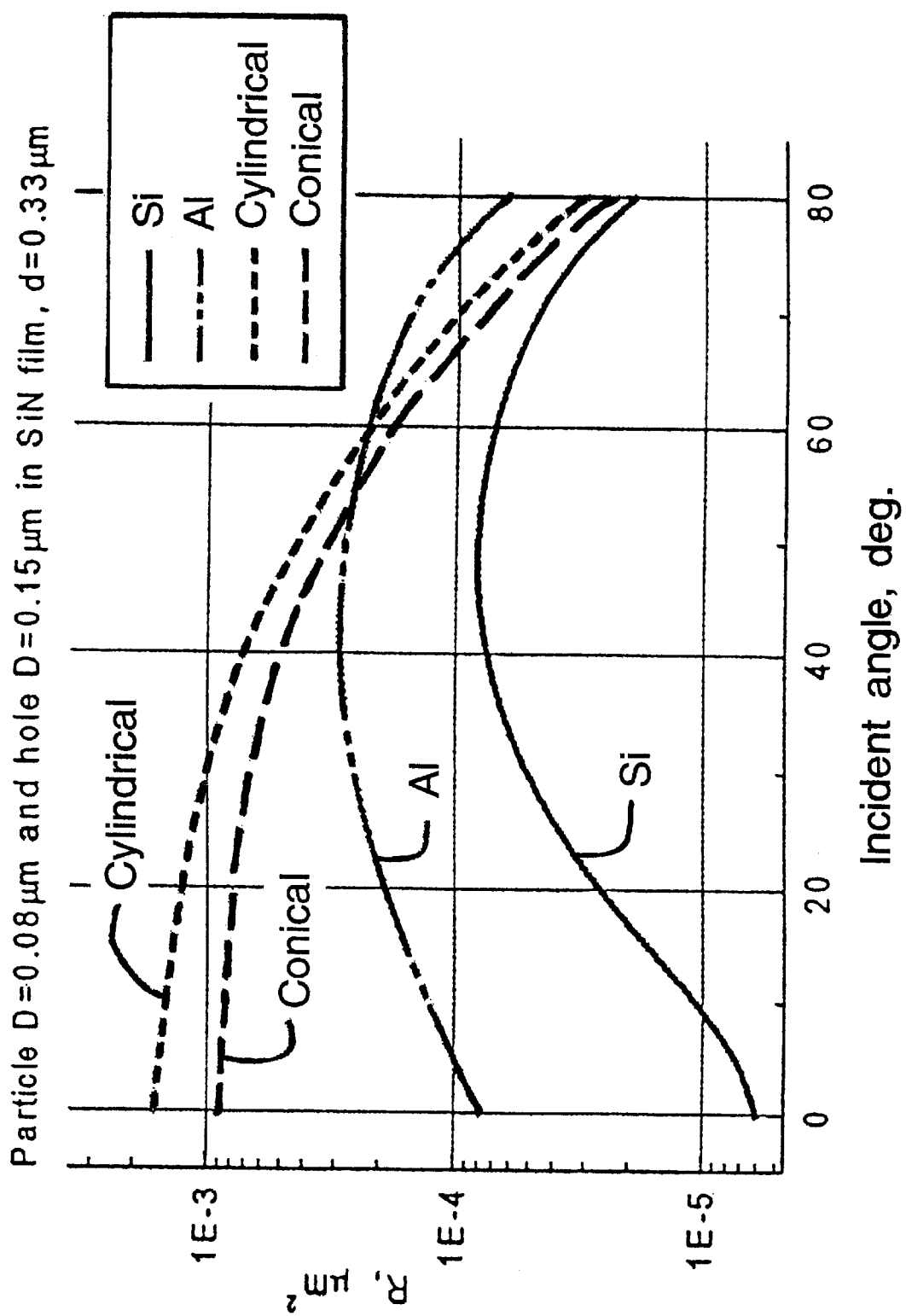
FIGS. 3a–d show computer simulation results plotting a response function comprising an area integral of the DSC distribution over a range of scattering angles and azimuth angles, comparing response functions of 0.08 μm-diameter particles with those of 0.15 μm-diameter holes as a function of incident angle.
Figure 3B:
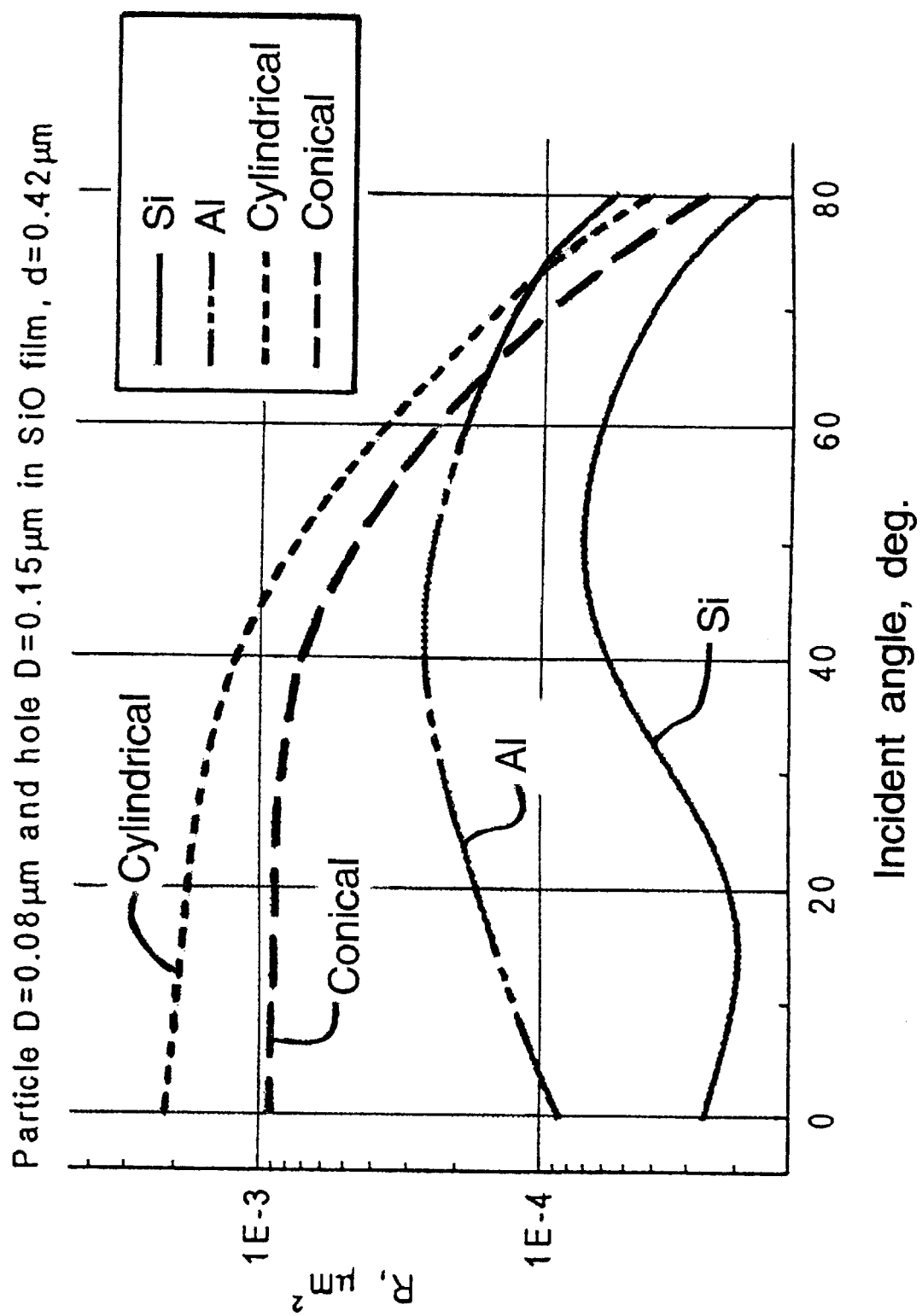
Figure 3C:
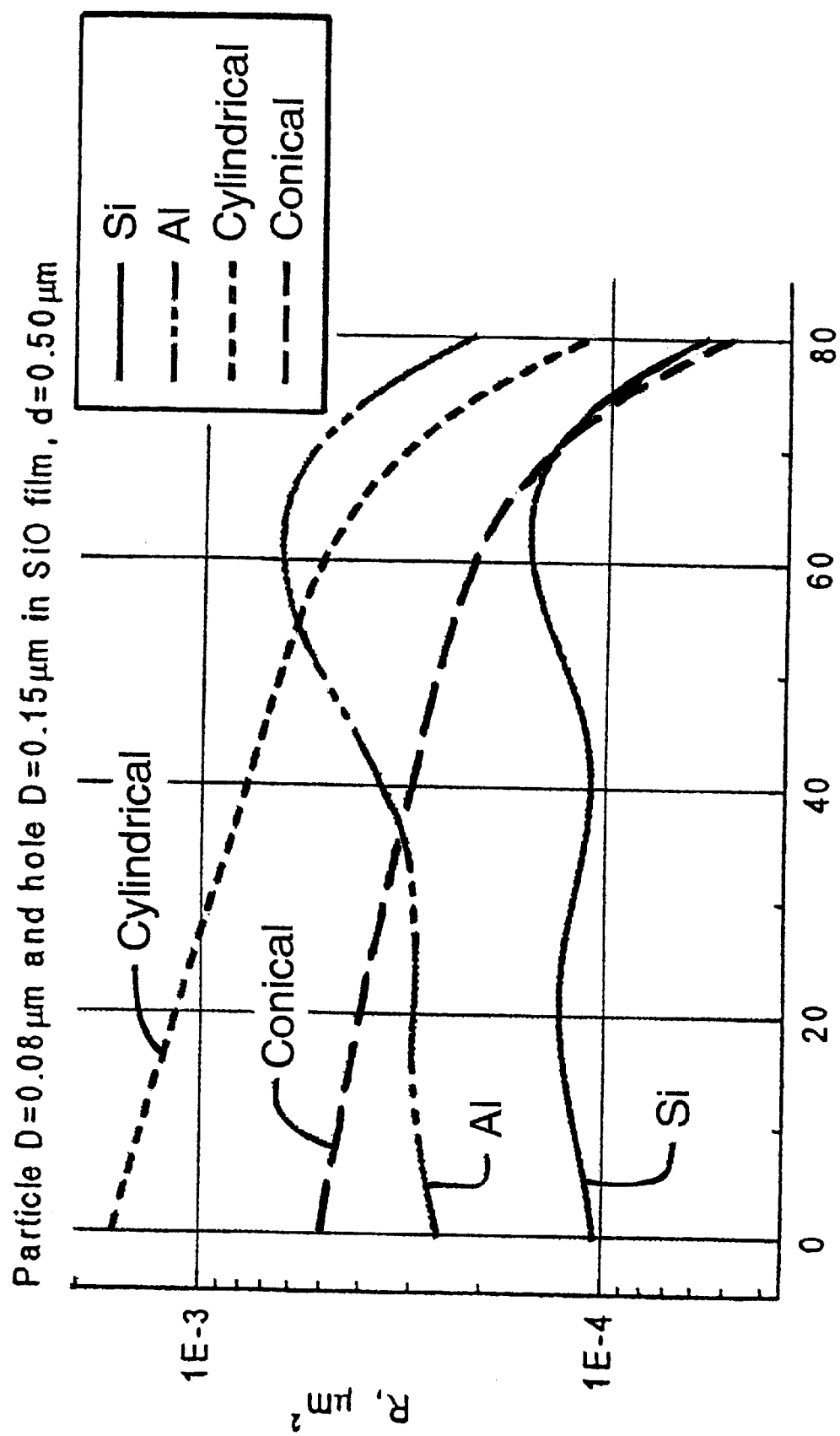
Figure 3D:
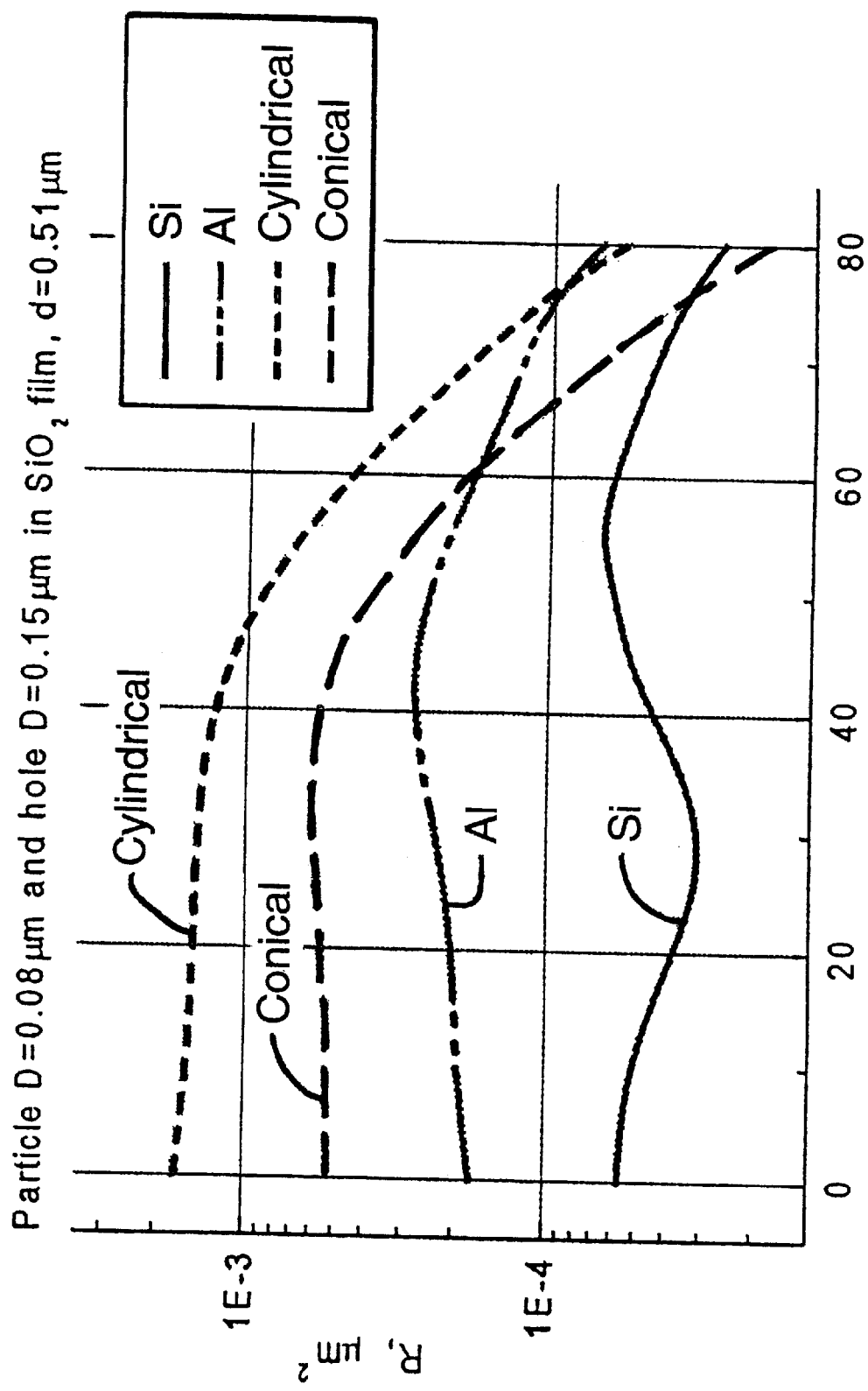
Figure 4:
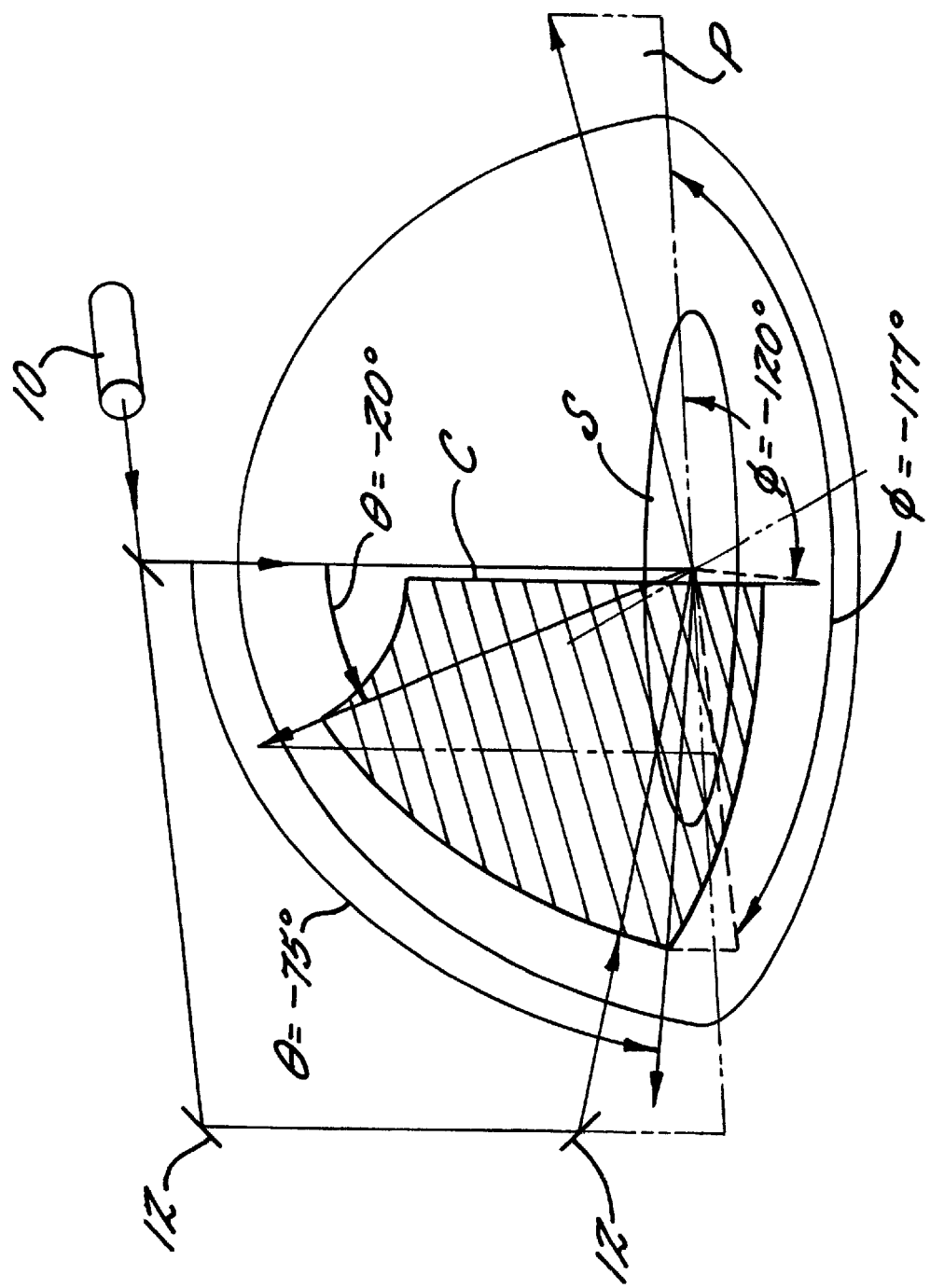
FIG. 4 is a schematic perspective view of an apparatus suitable for carrying out a method for discriminating between holes and particles on a filmed substrate in accordance with the present invention.

FIG. 3a shows the response function $R^P$ versus incident angle corresponding to scattering on Si or Al spheres (D=0.08 $\mu$m) and cylindrical or conical holes in a SiN film of thickness d=0.33 $\mu$m. FIG. 3b shows similar results for a SiO film of thickness d=0.42 $\mu$m. Responses concerned with a non-resonance SiO film thickness d=0.50 $\mu$m are depicted on FIG. 3c. Results corresponding to a SiO2 film of thickness d=0.51 $\mu$m are shown on FIG. 3d.

Summarizing these results, it is seen that the P-polarized response function $R^P$ versus incident angle for a hole rapidly decreases over the whole range of incidence. In contrast, the response for a particle does not exhibit any substantial decrease, and in some cases actually increases slightly from normal incidence ($\theta_0=0°$) to highly oblique incidence angles. Thus, based on the model results, it should be possible to discriminate a particle from a hole by measuring $R^P$ for both a normal (or near normal) incidence and an oblique incidence (e.g., −65°). If the response for the oblique incidence is substantially lower than that for the normal incidence, then the defect can be classified as a hole; if the two responses are not greatly different, then the defect can be classified as a particle.

It should be noted that although the collector area $\phi$ used in the computer simulations was discontinuous, being made up of two separate areas each generally configured as half of a semi-annular ring, it is expected that similar results can be obtained by using a single collector, for example formed as a semi-annular ring symmetrically placed with respect to the incident plane. In this case, the incident beam can be directed to pass beneath the lower edge of the collector. For instance, a collector can be configured to cover a range of scattering angles $\theta$ of about −20° to −70°, and the incident beam can be directed at an incident angle sufficiently greater than −70° (e.g., −75°) so that the lower edge of the collector does not interfere with the incident beam. Other collector types and geometries can also be used, including plural collectors of various sizes and/or shapes distributed about the back half of the hemisphere in various positions, in order to collect back-scattered light over a wide area. For instance, the collector C can be formed as a mirror and configured to reflect and focus the collected light onto a detector such as a photomultiplier tube or the like. Alternatively, one or more lenses can be used for focusing light onto one or more detectors. Additionally, it will be understood that signal discrimination circuitry (not shown) can be provided for comparing the intensities of light produced by the two different incident angles and for classifying a defect as a hole or a particle based on the comparison of the intensities.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for detecting defects on a surface of a film-covered substrate and for discriminating between particles on the film and holes in the film, the method comprising:
    directing a first beam of light having a predominant P-polarized component onto the substrate at a first incident angle such that the light is scattered by any defect present at or in the film;
    detecting a first intensity of light back-scattered over one or more regions of space caused by the first beam;
    directing a second beam of light having a predominant P-polarized component onto the substrate at a second incident angle that is angularly displaced substantially farther from a surface normal than the first beam;
    detecting a second intensity of light back-scattered over said one or more regions caused by the second beam; and
    classifying a detected defect as either a particle on the film or a hole in the film based on relative magnitudes of the first and second intensities.

2. The method of claim 1, wherein the first incident angle is about 0° and the second incident angle is angularly displaced from the surface normal by at least about 60°.

3. The method of claim 1, wherein the back-scattered light is collected over a range of scattering angles at least about 40° wide.

4. The method of claim 1, wherein the back-scattered light is collected over a range of azimuth angles at least about 40° wide.

5. The method of claim 1, wherein the back-scattered light is collected over a generally semi-annular region disposed symmetrically with respect to an incident plane containing the two incident beams.

6. The method of claim 1, wherein a defect is classified as a hole in the film when the first intensity of the back-scattered light caused by the first beam is substantially larger than the second intensity of the back-scattered light caused by the second beam.

7. The method of claim 6, wherein the first beam is directed onto the substrate at a generally normal incidence angle and the second beam is directed onto the substrate at an incidence angle displaced at least about 60° from normal.

* * * * *